(12) United States Patent
Han et al.

(10) Patent No.: US 7,816,351 B2
(45) Date of Patent: Oct. 19, 2010

(54) 5,6-DIMETHYLTHIENO[2,3-DI] PYRIMIDINE DERIVATIVES, THE PREPARATION METHOD THEREOF AND THE PHARMACEUTICAL COMPOSITION COMPRISING THE SAME FOR ANTI-VIRUS

(75) Inventors: Cheol Kyu Han, Seoul (KR);
Jeonghyeok Yoon, Yongin-si (KR);
Nam-Doo Kim, Incheon-si (KR); Jin-ah Kim, Taejeon-si (KR)

(73) Assignee: Equispharm Co., Ltd, Daejeon (KR)

( * ) Notice: Subject to any disclaimer, the term of this patent is extended or adjusted under 35 U.S.C. 154(b) by 354 days.

(21) Appl. No.: 12/067,246

(22) PCT Filed: Sep. 23, 2005

(86) PCT No.: PCT/KR2005/003172

§ 371 (c)(1),
(2), (4) Date: Mar. 18, 2008

(87) PCT Pub. No.: WO2007/035010

PCT Pub. Date: Mar. 29, 2007

(65) Prior Publication Data

US 2008/0234482 A1    Sep. 25, 2008

(51) Int. Cl.
*A61K 31/5377* (2006.01)
*C07D 413/14* (2006.01)
(52) U.S. Cl. .................................. 514/234.5; 544/119
(58) Field of Classification Search ................ 544/119; 514/234.5
See application file for complete search history.

(56) References Cited

U.S. PATENT DOCUMENTS 6,133,271 A    10/2000   Pamukcu et al.

FOREIGN PATENT DOCUMENTS

EP    82023 A    6/1983
WO    2005047292 A    5/2005

OTHER PUBLICATIONS

Davis, et al. "Treatment of Chronic Hepatitis C with Recombinant Interferon Alfa; A Multicenter Randomized, Controlled Trial" New England Journal of Medicine, 321, 1501, 1989.
Harvey J. Alter "Chronic Consequences of Non-A, Non-B Hepatitis" Current Persepective in Hepatology, p. 83, 1989.

*Primary Examiner*—Rebecca L Anderson
(74) *Attorney, Agent, or Firm*—Lucas & Mercanti, LLP

(57) ABSTRACT

Disclosed herein are 5,β-dimethylthieno[2,3-d]pyrimidine derivatives useful as antiviral agents. More particularly, disclosed are 5,β-dimethylthieno[2,3-d]pyrimidine derivatives represented by Formula 1, having an excellent inhibitory effect on the proliferation of hepatitis C virus (HCV), pharmaceutically acceptable salts thereof, a preparation method thereof, and a pharmaceutical composition for the prevention and treatment of hepatitis C virus (HCV), containing, as active ingredients, these compounds. The 5,6-dimethylthieno [2,3-d]pyrimidine derivatives represented by Formula 1 have an excellent effect of inhibiting the proliferation of hepatitis C virus and also have low toxicity. Thus, these compounds are available as agents for the prevention and treatment of hepatitis C.

4 Claims, No Drawings

5,6-DIMETHYLTHIENO[2,3-DI] PYRIMIDINE DERIVATIVES, THE PREPARATION METHOD THEREOF AND THE PHARMACEUTICAL COMPOSITION COMPRISING THE SAME FOR ANTI-VIRUS

CROSS-REFERENCE TO RELATED APPLICATIONS

This application is a 371 of PCT/KR2005/003172 filed on Sep. 23, 2005, the contents of which are incorporated herein by reference.

TECHNICAL FIELD

The present invention relates to a 5,6-dimethylthieno[2,3-d]pyrimidine derivative useful as antiviral agents, and more particularly to a pharmaceutical composition for the prevention and treatment of hepatitis C, which contains, as an active ingredient, a novel 5,6-dimethylthieno[2,3-d]pyrimidine derivative having an excellent inhibitory effect on the proliferation of hepatitis C virus.

BACKGROUND ART

Hepatitis C virus (HCV) is a membrane-containing virus belonging to the Flavivirus family. The genome thereof is (+)-RNA (plus-strand RNA), which is 9.6 kb in length and expresses a poly-protein consisting of 3,010 amino acids. The poly-protein is separated into 3 structural proteins and 6 nonstructural proteins by its host cell and viral enzyme.

The 5' and 3' termini of the HCV genome have non-translated regions in which base sequences of almost all genotypes are highly conserved. 330-341 nucleotides at the 5' terminus, and 98 nucleotides downstream of poly A at the 3' terminus, were recently found, which are thought to play an important role in the RNA replication or translation of the virus. The amino terminus end of the viral genome makes viral structural proteins, a core, E1 and E2, and the remaining region makes nonstructural proteins. The core gene consists of a viral capsid protein, and E1 and E2 consist of viral coat proteins. These proteins are released from each other by a signal peptidase in the endoplasmic reticulum. The nonstructural proteins are processed by serine protease NS3 and cofactor NS4A. NS5B is an enzyme which functions as RNA-dependent RNA polymerase and is most important in the replication of the virus.

Infection with HCV occurs by blood transfusion and community-acquired infection, and there is a report that about 70% of HCV infection is caused by kidney dialysis. It is known that about 20% of HCV infection causes acute hepatitis accompanying liver cirrhosis within 5 years and progresses to liver cancer (see Davis et al, New. Engl. J. Med., 321, 1501, 1989; Alter et al, in Current Perspective in Hepatology, p 83, 1989). Such a high chronic infection rate is rare in RNA viruses and shows that HCV is a mediator that causes a high rate of liver cancer. There is still no study on the mechanism of continuous infection with HCV. Recently, HCV infection caused by blood transfusion has been significantly decreased, because HCV tests are sufficiently conducted for all blood, however, community-acquired HCV infection cannot yet be controlled, and thus becomes an important problem worldwide.

In epidemiological terms, HCV is uniformly distributed worldwide, unlike HBV, and it is reported that 1.5-2% of the worldwide population has HCV-infection. HCV infection progresses to chronic hepatitis, and the probability of progression of HCV infection to liver cirrhosis and liver cancer is significantly higher than that of infection with hepatitis B virus. Because hepatitis C virus belongs to a completely different viral family, from that of hepatitis B virus in terms of taxonomy, it is impossible to prevent hepatitis C virus with hepatitis B virus vaccine. Also, although there is an attempt to treat hepatitis C virus with $\alpha$-IFN, a response to $\alpha$-IFN significantly varies depending on the genotype of hepatitis C virus, and the effect of this treatment method is very insignificant. Particularly, in the case of genotype 1b with which many persons are infected, the therapeutic effect of $\alpha$-IFN is most insignificant.

Since the RNA genome of HCV was first isolated by cloning in the year 1989, many studies on HCV have been conducted, but an effective therapeutic drug against HCV is not yet developed. As a therapeutic agent against HCV infection, interferon in combination with antiviral drug ribavirin is currently used, but it has an insignificant effect, because it has a low cure rate and shows side effects. Thus, additional compounds for the treatment and prevention of HCV infection have been required.

Accordingly, the present inventors have made efforts to develop compounds having low side effects and toxicity and showing excellent antiviral activity against HCV and, as a result, found that 5,6-dimethylthieno[2,3-d]pyrimidine derivatives represented by Formula 1 below have an excellent inhibitory effect on the proliferation of HCV.

DISCLOSURE

Technical Problem

An object of the present invention is to provide 5,6-dimethylthieno[2,3-d]pyrimidine derivatives.

Another object of the present invention is to provide a method for preparing 5,6-dimethylthieno[2,3-d]pyrimidine derivatives.

Still another object of the present invention is to provide a pharmaceutical composition for the prevention and treatment of hepatitis C, which contains 5,6-dimethylthieno[2,3-d]pyrimidine derivatives and has an excellent inhibitory effect on the proliferation of hepatitis C virus (HCV).

Technical Solution

To achieve the above objects, the present invention provides 5,6-dimethylthieno[2,3-d]pyrimidine derivatives.

Also, the present invention provides a method for preparing 5,6-dimethylthieno[2,3-d]pyrimidine derivatives.

In addition, the present invention provides a pharmaceutical composition for the prevention and treatment of hepatitis C, which contains 5,6-dimethylthieno[2,3-d]pyrimidine derivatives and has an excellent inhibitory effect on the proliferation of hepatitis C virus (HCV).

ADVANTAGEOUS EFFECTS

The novel 5,6-dimethylthieno[2,3-d]pyrimidine derivatives according to the present invention have an excellent effect of inhibiting the proliferation of hepatitis C virus and also have low toxicity. Thus, these compounds are available as agents for the prevention and treatment of hepatitis C.

BEST MODE

Hereinafter, the present invention will be described in detail.

The present invention provides 5,6-dimethylthieno[2,3-d]pyrimidine derivatives represented by Formula 1:

[Formula 1]

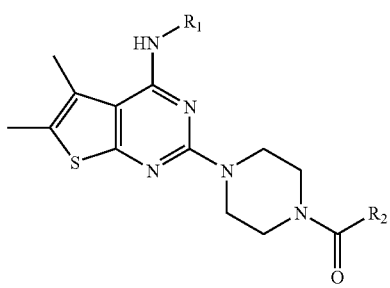

wherein $R_1$ represents

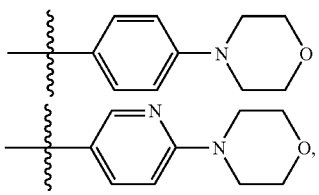

and $R_2$ represents

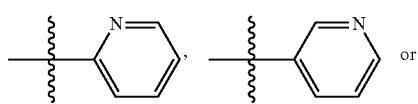  or  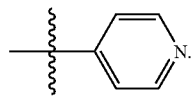

The inventive compounds of Formula 1 according to the present invention can be used in the form of pharmaceutically acceptable salts. As the salts, acid addition salts formed with pharmaceutically acceptable free acids are useful. The compounds of Formula 1 can be formed into pharmaceutically acceptable acid addition salts according to any conventional method known in the art. Free acids, which can be used in the present invention, include organic and inorganic acids. The inorganic acids include hydrochloric acid, bromic acid, sulfuric acid, phosphoric acid and the like, and the organic acids include citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, p-toluenesulfonic acid, glutamic acid, aspartic acid and the like.

In another aspect, the present invention provides a method for preparing a 5,6-dimethylthieno[2,3-d]pyrimidine derivative according to Reaction Scheme 1, the method comprising the steps of:

1) allowing 2,4-dichloro-5,6-dimethyl-thieno[2,3-d]pyrimidine of compound 2 in Reaction Scheme 1 to react with substituted aniline of compound 3 to obtain 2-chloro-5,6-dimethyl-thieno[2,3-d]-pyrimidine of compound 4 having an aniline derivative substituted at position 4;

2) allowing said compound 4 to react with piperazine of compound 5 to obtain compound 6; and 3) allowing said compound 6 to react with compound 7 to obtain a 5,6-dimethylthieno[2,3-d]pyrimidine derivative of Formula 1:

[Reaction Scheme 1]

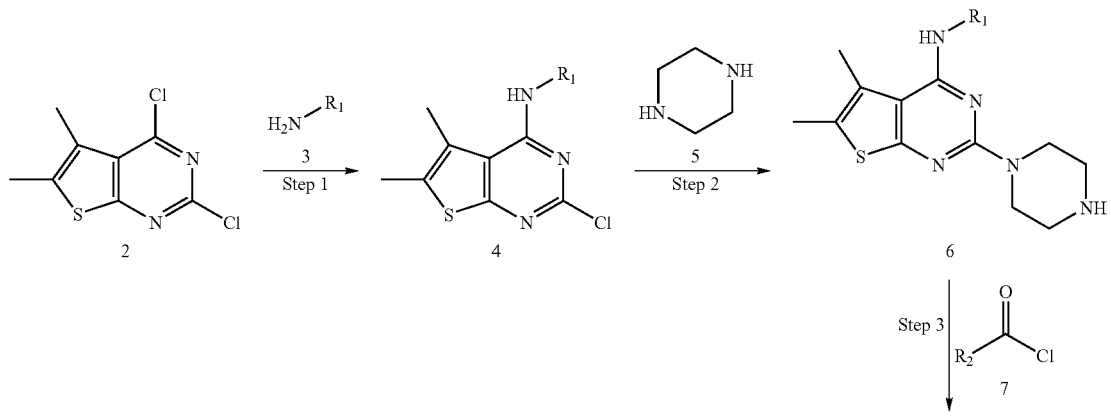

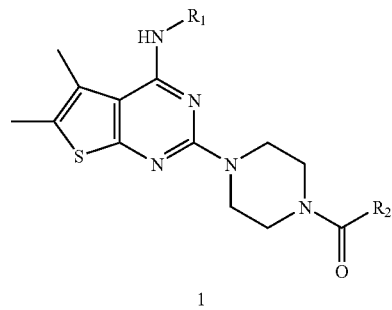

wherein,

R₁ represents

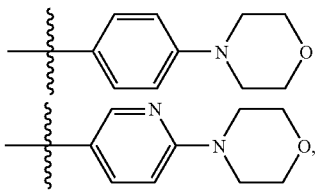

and R₂ represents

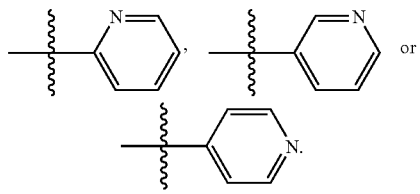

Examples of a reaction solvent, which can be used in said preparation method, include organic solvents such as methanol, ethanol, isopropanol, dichloromethane, chloroform, acetonitrile, N,N-dimethylformamide, acetone and the like. The reaction in the preparation method is preferably carried out at a temperature of 0-150° C. for 2-20 hours in said solvent in the presence of a general organic base such as triethylamine, N,N-diisopropylethylamine, N-methylmorpholine, 1-methylpiperidine, pyridine, 2,6-lutidine, 4-dimethylaminopyridine, or N,N-dimethylaniline.

In still another aspect, the present invention provides a pharmaceutical composition for the treatment or prevention of hepatitis C, which contains, as active ingredients, a 5,6-dimethylthieno[2,3-d]pyrimidine derivative of Formula 1 and/or pharmaceutically acceptable salt thereof.

The compounds of Formula 1 according to the present invention can be administered orally or parenterally for the treatment of hepatitis C in clinical applications and can be used in the form of general drug formulations. Specifically, the inventive compounds of Formula 1 can be administered in the form of oral or parenteral (preferably, injection) formulations in actual clinical applications. The inventive compounds are formulated using general diluents or excipients such as general fillers, carriers, binders, wetting agents, disintegrants and surfactants. Solid formulations for oral administration include tablets, pills, powders, granules, and capsules, and are prepared by mixing the compound of Formula 1 with at least one excipient, for example, starch, calcium carbonate, sucrose, lactose or gelatin. Liquid formulations for oral administration include suspensions, solutions, emulsions, syrup and the like, and may contain various excipients, for example, wetting agents, flavoring agents, aromatics and preservatives, in addition water and liquid paraffin, which are frequently used simple diluents. Formulations for parenteral administration include sterilized aqueous solutions, nonaqueous solvents, suspending agents, emulsifying agents and the like. Examples of nonaqueous solvents and suspending agents, which can be used in the present invention, include vegetable oils such as propylene glycol, polyethylene glycol and olive oil, and injectable ester such as ethyl oleate.

Although the effective dosage of the inventive compounds of Formula 1 can be suitably selected depending on the sex, age and condition of patients, the inventive compounds can generally be administered to adults in a dosage of 10-1000 mg/day, and preferably 20-500 mg/day, 1-3 times a day.

MODE FOR INVENTION

Hereinafter, the present invention will be described in further detail with reference to examples and test examples. It is to be understood, however, that these examples are for illustrative purposes only and are not to be construed to limit the scope of the present invention.

EXAMPLE 1

Preparation of 4-[5,6-dimethyl-4-(4-morpholin-4-yl-phenylamino)-thieno[2,3-d]pyrimidin-2-yl]-piperazin-1-yl-pyridin-2-yl-methanone To 240 mg (1.02 mmol of 2,4-dichloro-5,6-dimethyl-thieno[2,3-d]pyrimidine in 50 ml of ethyl alcohol were added 220.20 mg (1.23 mmol) of 4-(4-morpholino)aniline and 130.90 mg (1.23 mmol) of aniline, and then the mixture was stirred under reflux. After completion of the reaction, the reaction solvent, ethyl alcohol, was evaporated under reduced pressure, and the residue was crystallized from ethyl alcohol and filtered, yielding 430 mg (quantitative) of 2-chloro-5,6-dimethyl-thieno[2,3-d]pyrimidin-4-yl-4-morpholin-4-yl-phenylamine. 220 mg (0.53 mmol) of the obtained product was dissolved in 20 ml of 1-butanol in a sealed tube, and 223 µl (1.59 mmol) of triethylamine and 45.9 mg of piperazine were added thereto, and the mixture was stirred at 120° C. After completion of the reaction, the resulting solid was filtered and the filtrate was concentrated under reduced pressure and then crystallized from ethyl acetate, yielding 30 mg (15% yield) of 5,6-dimethyl-2-piperazin-1-yl-thieno[2,3-d]pyrimidin-4-yl-4-morpholin-4-yl-phenylamine. To 9 mg (0.02 mmol) of the obtained compound and 5,6-dimethyl-2-piperazin-1-yl-thieno[2,3-d]pyrimidin-4-yl-4-morpholin-4-yl-phenylamine in 5 ml of dimethyl chloride were added 3.5 µl (0.02 mmol) of triethylamine and 4.1 mg (0.02 mmol) of picolinoyl chloride hydrochloride, and then the mixture was stirred at room temperature for 3 hours. After completion of the reaction, the reaction solvent, dimethyl chloride, was evaporated under reduced pressure, and the residue was crystallized from dimethyl chloride, thus obtaining 6 mg (30% yield) of the title product.

$^1$H NMR (CDCl$_3$) ppm: 8.85-8.95 (d, 1H), 8.27-8.35 (m, 1H), 7.79-8.01 (m, 1H), 7.60-7.79 (m, 1H), 7.25-7.30 (m, 2H), 6.87-6.95 (m, 2H), 3.92-3.70 (m, 10H), 3.40 (br, 2H), 3.18-3.13 (t, J=3.4 Hz, 4H), 2.50 (s, 3H), 2.37 (s, 3H).

EXAMPLE 2

Preparation of 4-[5,6-dimethyl-4-(4-morpholin-4-yl-phenylamino)-thieno[2,3-d]pyrimidin-2-yl]-piperazin-1-yl-pyridin-3-yl-methanone The title product (45% yield) was obtained in the same manner as in Example 1, except that nicotinoyl chloride hydrochloride was used in the place of picolinoyl chloride hydrochloride.

$^1$H NMR (CDCl$_3$) ppm: 9.20 (s, 1H), 8.99-9.05 (m, 1H), 8.88-8.99 (m, 1H), 8.11-8.30 (m, 1H), 7.25-7.38 (d, 2H), 6.85-6.95 (d, 2H), 3.92-3.76 (m, 10H), 3.42 (br, 2H), 3.18-3.14 (t, J=3.4 Hz, 4H), 2.53 (s, 3H), 2.39 (s, 3H).

EXAMPLE 3

Preparation of 4-[5,6-dimethyl-4-(4-morpholin-4-yl-phenylamino)-thieno[2,3-d]pyrimidin-2-yl]-piperazin-1-yl-pyridin-4-yl-methanone The title product (48% yield) was obtained in the same manner as in Example 1, except that isonicotinoyl chloride hydrochloride was used in the place of picolinoyl chloride hydrochloride.

$^1$H NMR (CDCl$_3$) ppm: 8.75 (d, J=5.6 Hz, 2H), 7.46 (d, J=9.0 Hz, 2H), 7.34 (d, J=1.6 Hz, 2H), 7.04 (s, 1H), 6.93 (d, J=8.8 Hz, 2H), 3.92-3.76 (m, 10H), 3.41 (br, 2H), 3.19-3.14 (t, J=3.4 Hz, 4H), 2.51 (s, 3H), 2.39 (s, 3H)

EXAMPLE 4

Preparation of 4-[5,6-dimethyl-4-(6-morpholinopyridin-3-ylamino)-thieno[2,3-d]pyrimidin-2-yl]-piperazin-1-yl-pyridin-2-yl-methanone To 240 mg (1.02 mmol) of 2,4-dichloro-5,6-dimethyl-thieno[2,3-d]-pyrimidine in 50 ml of ethyl alcohol were added 226.40 mg (1.26 mmol) of 6-morpholinopyridin-3-amine and 130.90 mg (1.23 mmol) of calcium carbonate, and then the mixture was stirred under reflux. After completion of the reaction, the reaction solvent, ethyl alcohol, was evaporated under reduced pressure, and the residue was crystallized from ethyl alcohol and filtered, yielding 440 mg (quantitative) of 2-chloro-5,6-dimethyl-N-(6-morpholinopyridin-3-yl)-thenio[2,3-d]pyrimidine-4-amine. 200 mg (0.50 mmol) of the obtained product was dissolved in 20 ml of 1-butanol in a sealed tube, and 220 µl (1.50 mmol) of triethylamine and 45.9 mg of piperazine were added thereto, and the mixture was stirred at 120° C. After completion of the reaction, the resulting solid was filtered and the filtrate was concentrated under reduced pressure and then crystallized from ethyl acetate, yielding 25 mg (12% yield) of 5,6-dimethyl-N-(6-morpholinopyridin-3-yl)-2-(piperazin-1-yl)thieno[2,3-d]pyrimidine-4-amine. To 9 mg (0.02 mmol) of the obtained compound, 5,6-dimethyl-2-piperazin-1-yl-thieno[2,3-d]pyrimidin-4-yl-4-morpholin-4-yl-phenylamine in 5 ml of dimethyl chloride were added 3.5 µl (0.02 mmol) of triethylamine and 4.1 mg (0.02 mmol) of picolinoyl chloride hydrochloride, and then the mixture was stirred at room temperature for 3 hours. After completion of the reaction, the reaction solvent, dimethyl chloride, was evaporated under reduced pressure and crystallized from ethyl acetate, thus obtaining 7 mg (35% yield) of the title product.

$^1$H NMR (CDCl$_3$) ppm: 9.05 (s, 1H), 8.85-8.95 (d, 1H), 8.27-8.35 (m, 1H), 7.79-8.01 (m, 1H), 7.60-7.79 (m, 1H), 7.25-7.30 (m, 1H), 6.87-6.95 (m, 1H), 3.72-3.50 (m, 8H), 3.22-3.45 (m, 8H), 2.40 (s, 3H), 2.27 (s, 3H), 1.59-1.51 (m, 6H)

EXAMPLE 5

Preparation of 4-[5,6-dimethyl-4-(6-morpholinopyridin-3-ylamino)-thieno[2,3-d]pyrimidin-2-yl]-piperazin-1-yl-pyridin-3-yl-methanone The title compound (35% yield) was prepared in the same manner as in Example 4, except that nicotinoyl chloride hydrochloride was used in place of picolinoyl chloride hydrochloride.

$^1$H NMR (CDCl$_3$) ppm: 9.17 (s, 1H), 8.85-8.95 (d, 1H), 8.27-8.35 (m, 1H), 7.79-8.01 (m, 1H), 7.60-7.79 (m, 1H), 6.99-6.99 (d, 1H), 6.65-6.77 (d, 1 h), 3.51-3.70 (m, 8H), 3.23-3.46 (m, 8H), 2.41 (s, 3H), 2.25 (s, 3H), 1.59-1.52 (m, 6H)

EXAMPLE 6

Preparation of 4-[5,6-dimethyl-4-(6-morpholinopyridin-3-ylamino)-thieno[2,3-d]pyrimidin-2-yl]-piperazin-1-yl-pyridin-4-yl-methanone The title compound (42% yield) was prepared in the same manner as in Example 4, except that isonicotinoyl chloride hydrochloride was used in place of picolinoyl chloride hydrochloride.

$^1$H NMR (CDCl$_3$) ppm: 9.17 (s, 1H), 8.85-8.92 (d, 2H), 7.83-8.01 (d, 2H), 6.99-6.79 (d, 1H), 6.77-6.65 (d, 1H), 3.70-3.51 (m, 8H), 3.22-3.47 (m, 8H), 2.45 (s, 3H), 2.27 (s, 3H), 1.56-1.58 (m, 6H)

EXPERIMENTAL EXAMPLE 1

Results of HCV Replicon Inhibition Tests

In order to examine the HCV replicon inhibitory activities of the inventive 5,6-dimethylthienyl[2,3-d]pyrimidine derivatives represented by Formula 1, the following test was performed.

Replicon used to test HCV inhibitory activity was NK-R2AN consisting of HCV IRES, neomycin resistance gene, FMDV 2A protease, renilla luciferase, EMCV IRES, HCV nonstructural proteins NS3 to NS5B, and HCV 3' non-translated region (NTR). Liver cancer cell line Huh-7 containing hepatitis C virus replicon NK-R2AN was dispensed into each plate of a 24-well plate at a density of about 30,000 cells, and was cultured in a $CO_2$ incubator at 37° C. for 24 hours so as to fix the cells to the plate bottom. The culture medium was a DMEM animal cell culture medium containing 10% fetal bovine serum and 1% penicillin streptomycin. Compounds to be tested were dissolved in DMSO solvent and dispensed into each well at the desired concentration. Herein, the same amount of DMSO was added into each well, such that the final concentration of DMSO in each well was 0.5%. In DMEM animal cell culture media containing 2% fetal bovine serum and 1% penicillin streptomycin, the cells were cultured in a $CO_2$ incubator at 37° C. for 48 hours, and each of the media was removed by suction. After each well was washed with PBS solution, 60 µl of cell lysis-buffer for a Renilla luciferase assay was dispensed into each well, and the cells were cultured at room temperature for 30 minutes to lyse the cells.

5 µl of the cell lysis solution was added to 30 µl of a renilla luciferase substrate solution and measured for renilla luciferase activity. 20 µl of the cell lysis solution was subjected to a Bradford assay to measure the amount of proteins per unit cell lysis solution, and the renilla luciferase activity was divided by the protein amount measured through the Bradford assay to calculate the expression of reporters relative to cell mass. Using data on the proliferation of hepatitis C virus measured and the concentration of compound used, the results of hepatitis C virus inhibition were analyzed with the Prism4™ software (Graphpad).

Table 1 below shows the HCV replicon inhibitory test results measured using the above test method.

As described above, because the inventive compounds have an excellent effect of inhibiting the activity of hepatitis C virus (HCV), these compounds can be used to inhibit the proliferation of HCV. Thus, these compounds are available as agents for the prevention and treatment of hepatitis C.

EXPERIMENTAL EXAMPLE 2

Cytotoxicity Test

In order to examine whether the compounds of Formula 1 show cytotoxicity, these compounds were subjected to a widely known MTT assay in vitro using Hep G2 cells. As a result, it was found that the compounds used in the test all showed $CC_{50}$ values higher than 100 µg/ml, suggesting that these compounds had a very low cytotoxicity.

INDUSTRIAL APPLICABILITY

As described above, the novel 5,6-dimethylthieno[2,3-d]pyrimidine derivatives represented by Formula 1 according to the present invention have an excellent effect of inhibiting the proliferation of hepatitis C virus (HCV) and also have low toxicity. Thus, these compounds are available as agents for the prevention and treatment of hepatitis C.

TABLE

| Example | Substituents ($R_1$ and $R_2$) | HCV replicon inhibitory activity ($EC_{50}$) |
|---|---|---|
| Example 1 | 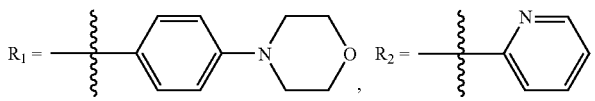 | 0.68 µM |
| Example 2 |  | 0.45 µM |
| Example 3 | 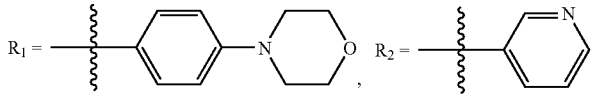 | 0.48 µM |
| Example 4 |  | 0.71 µM |
| Example 5 | 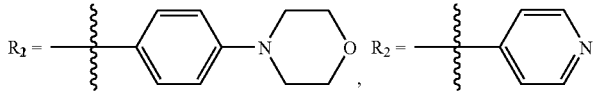 | 0.51 µM |
| Example 6 |  | 0.63 µM |

The invention claimed is:
1. A 5,6-dimethylthieno[2,3-d]pyrimidine compound of Formula 1:

[Formula 1]

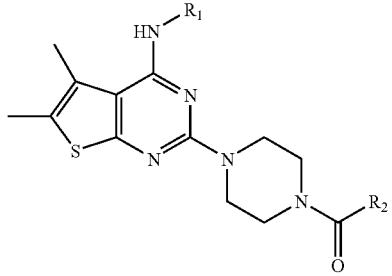

wherein
R₁ represents

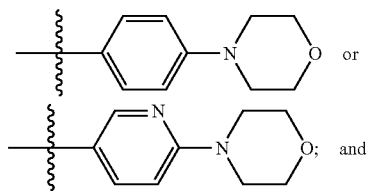

R₂ represents

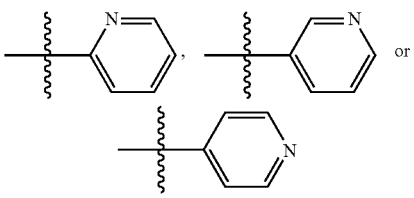

or a pharmaceutically acceptable salt thereof.

2. A method for preparing a 5,6-dimethylthieno[2,3-d]pyrimidine compound of Formula 1

[Formula 1]

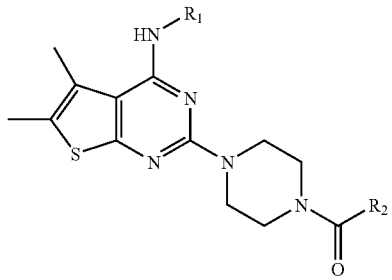

according to Reaction Scheme 1 comprising the steps of:
1) allowing 2,4-dichloro-5,6-dimethyl-thieno[2,3-d]pyrimidine of compound 2 to react with substituted aniline of compound 3 to obtain 2-chloro-5,6-dimethyl-thieno[2,3-d]-pyrimidine of compound 4 having an aniline derivative substituted at position 4;
2) allowing said compound 4 to react with piperazine of compound 5 to obtain compound 6; and
3) allowing said compound 6 to react with compound 7 to obtain a 5,6-dimethylthieno[2,3-d]pyrimidine compound of Formula 1:

[Reaction Scheme 1]

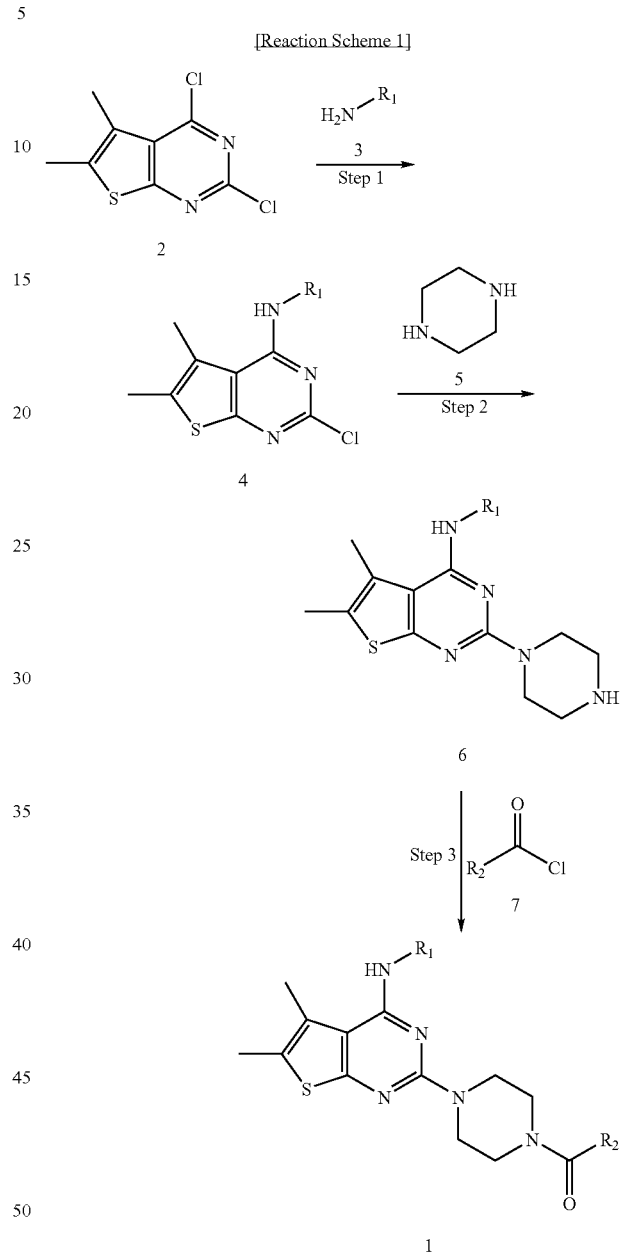

wherein
R₁ represents

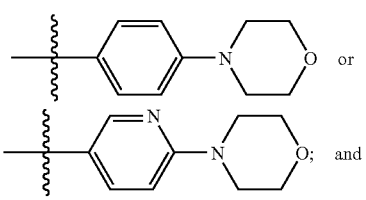

R₂ represents

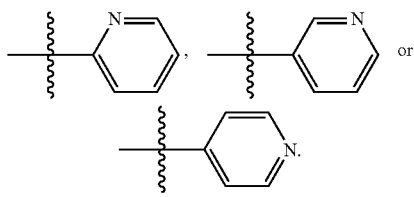

3. A pharmaceutical composition for the treatment of hepatitis C containing a 5,6-dimethylthieno[2,3-d]pyrimidine compound of claim 1 or a pharmaceutically acceptable salt thereof as an active ingredient.

4. A method for treating or preventing hepatitis C in a mammal comprising administering an effective amount of a 5,6-dimethylthieno[2,3-d]pyrimidine compound of claim 1 or a pharmaceutically acceptable salt thereof to a mammal in need thereof.

* * * * *